United States Patent

Veca et al.

[11] Patent Number: 6,053,923
[45] Date of Patent: Apr. 25, 2000

[54] METHOD AND APPARATUS FOR ABRADING TISSUE

[75] Inventors: John J. Veca, Alta Loma; Mark G. Sherfey, Pomona, both of Calif.

[73] Assignee: Arthrotek, Inc., Warsaw, Ind.

[21] Appl. No.: 09/040,003

[22] Filed: Mar. 17, 1998

[51] Int. Cl.[7] .................................................. A61B 17/00
[52] U.S. Cl. .............................................. 606/80; 606/79
[58] Field of Search .................................. 606/79, 80, 86, 606/88, 159, 167, 168, 170, 180; 604/19, 22, 902; 600/157, 565

[56] References Cited

U.S. PATENT DOCUMENTS

| | | |
|---|---|---|
| 3,732,858 | 5/1973 | Banko . |
| 3,844,272 | 10/1974 | Banko . |
| 3,902,498 | 9/1975 | Niederer . |
| 3,937,222 | 2/1976 | Banko . |
| 3,976,077 | 8/1976 | Kerfoot, Jr. . |
| 3,996,935 | 12/1976 | Banko . |
| 4,203,444 | 5/1980 | Bonnell et al. . |
| 4,274,414 | 6/1981 | Johnson et al. . |
| 4,320,761 | 3/1982 | Haddad . |
| 4,368,734 | 1/1983 | Banko . |
| 4,445,509 | 5/1984 | Auth . |
| 4,496,342 | 1/1985 | Banko . |
| 4,512,344 | 4/1985 | Barber . |
| 4,577,629 | 3/1986 | Martinez . |
| 4,598,710 | 7/1986 | Kleinberg et al. . |
| 4,603,694 | 8/1986 | Wheeler . |
| 4,646,738 | 3/1987 | Trott . |
| 4,649,919 | 3/1987 | Thimsen et al. . |
| 4,664,112 | 5/1987 | Kensey ..................................... 128/341 |
| 4,674,502 | 6/1987 | Imonti . |
| 4,705,038 | 11/1987 | Sjostrom et al. . |
| 4,811,734 | 3/1989 | McGurk-Burleson et al. . |
| 4,834,729 | 5/1989 | Sjostrom . |
| 4,842,578 | 6/1989 | Johnson et al. . |
| 4,844,064 | 7/1989 | Timsen et al. . |
| 4,850,354 | 7/1989 | McGurk-Burleson et al. . |
| 4,867,157 | 9/1989 | McGurk-Burleson et al. ........ 128/305 |
| 4,898,574 | 2/1990 | Uchiyama et al. . |
| 4,923,441 | 5/1990 | Shuler . |
| 4,950,278 | 8/1990 | Sachse et al. . |
| 4,994,067 | 2/1991 | Summers . |
| 5,007,917 | 4/1991 | Evans . |
| 5,074,841 | 12/1991 | Ademovic et al. . |
| 5,100,426 | 3/1992 | Nixon . |
| 5,112,299 | 5/1992 | Pascaloff . |
| 5,123,904 | 6/1992 | Shimomura et al. . |

(List continued on next page.)

FOREIGN PATENT DOCUMENTS

| | | |
|---|---|---|
| 1175725 | 10/1984 | Canada . |
| 808360 | 7/1951 | Germany . |
| 2 093 353 | 2/1982 | United Kingdom . |
| 2007239 | 5/1982 | United Kingdom . |
| 2 093 353 | 9/1982 | United Kingdom . |
| WO 92/15255 | 9/1992 | WIPO . |

OTHER PUBLICATIONS

MircoAire Advanced Surgical products, Arthroscopy Shaver Blades, Copyright 1991, 3 pages.
IES 1000 System—Arthrotek, pp. 6–8, Y–CAT–017C/093093.
Arthrotek, Inc.. IES 1000 Shaver Blades, ©copyright 1993, Arthrotek, Inc., 4 pages.
MicroAire Advanced Surgical Products, Arthroscopy Shaver Blades, ©copyright 1991, 3 pages.

*Primary Examiner*—Wynn Wood Coggins
*Assistant Examiner*—Jennifer Maynard
*Attorney, Agent, or Firm*—Harness, Dickey & Pierce, P.L.C.

[57] ABSTRACT

A method and apparatus for abrading tissue during arthroscopic surgery includes a first rotatable tube assembly and a second tube assembly. The first rotatably tube assembly has a first proximal end and a first distal end with an abrading head at the first distal end. The second tube assembly has a second proximal end and a second distal end with an external aspiration port passing through a sidewall of the second tube assembly. The apparatus further includes a self-cleaning mechanism which is operable to self-clean the aspiration port in the apparatus to pass fluid and debris.

17 Claims, 5 Drawing Sheets

U.S. PATENT DOCUMENTS

| | | |
|---|---|---|
| 5,160,318 | 11/1992 | Shuler . |
| 5,217,479 | 6/1993 | Shuler . |
| 5,226,909 | 7/1993 | Evans et al. . |
| 5,269,794 | 12/1993 | Rexroth . |
| 5,489,291 | 2/1996 | Wiley ................................. 606/170 |
| 5,490,860 | 2/1996 | Middle et al. . |
| 5,685,821 | 11/1997 | Pike . |

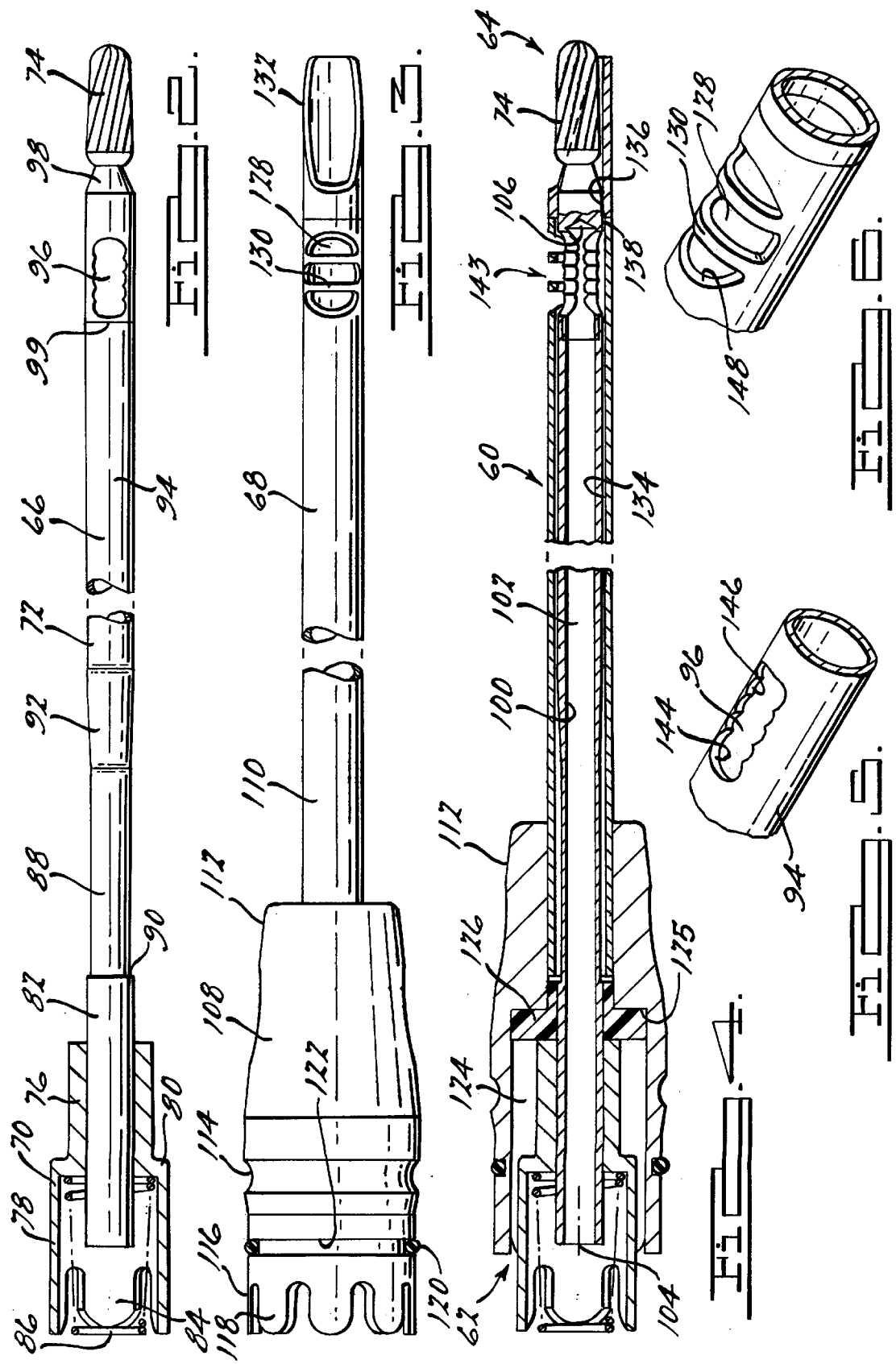

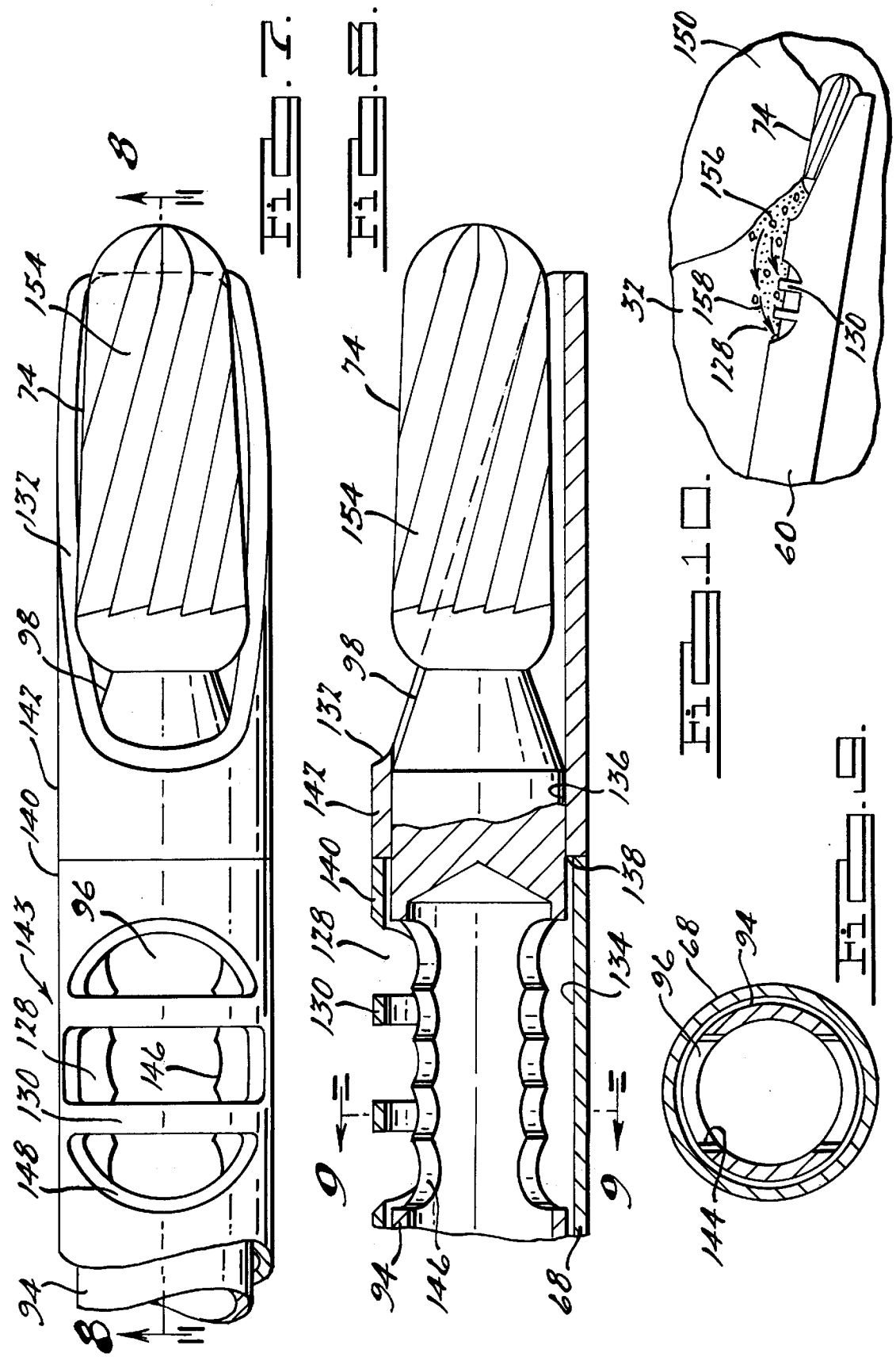

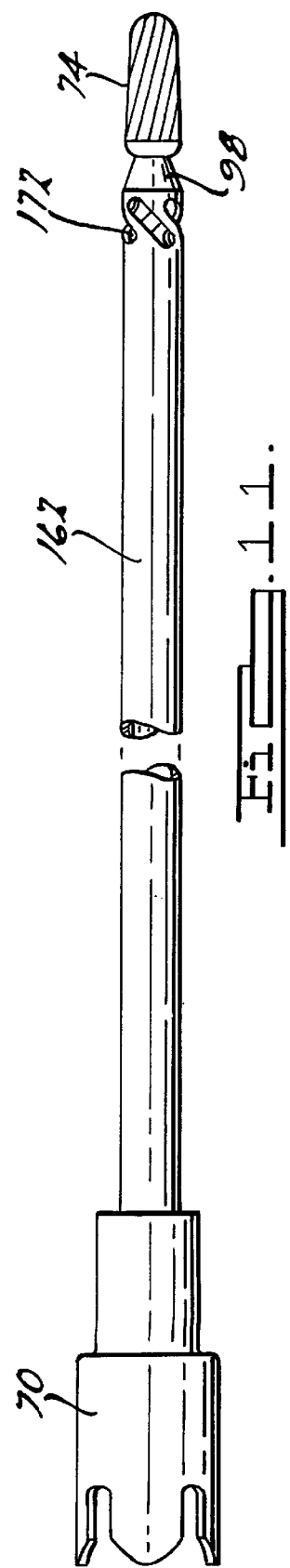
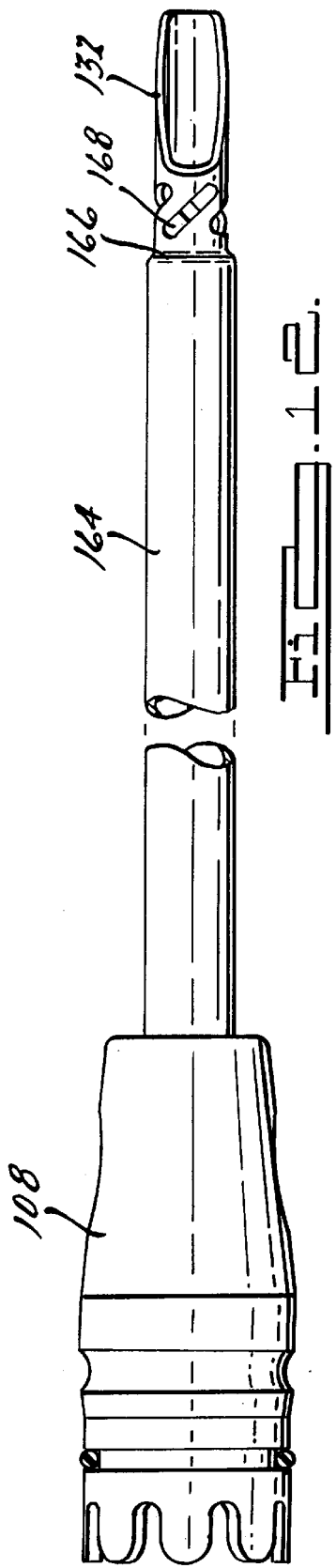
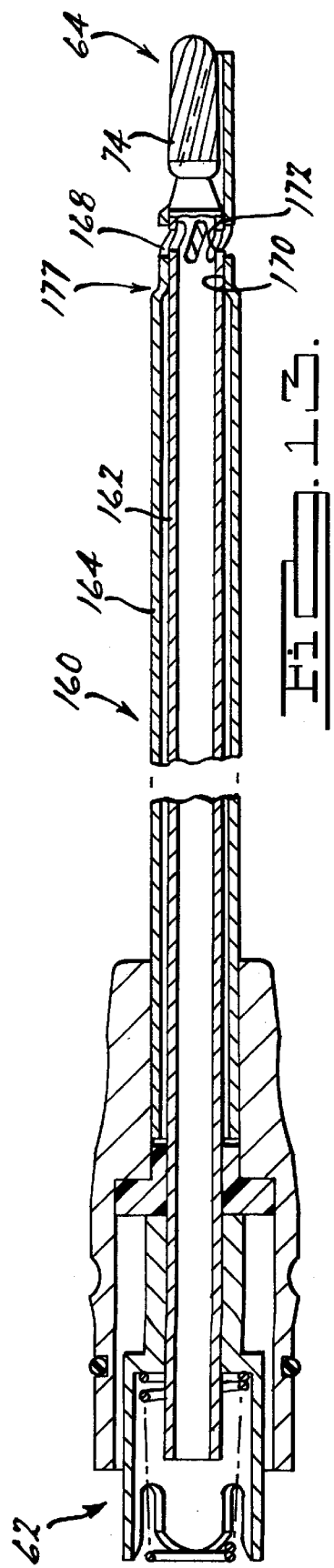

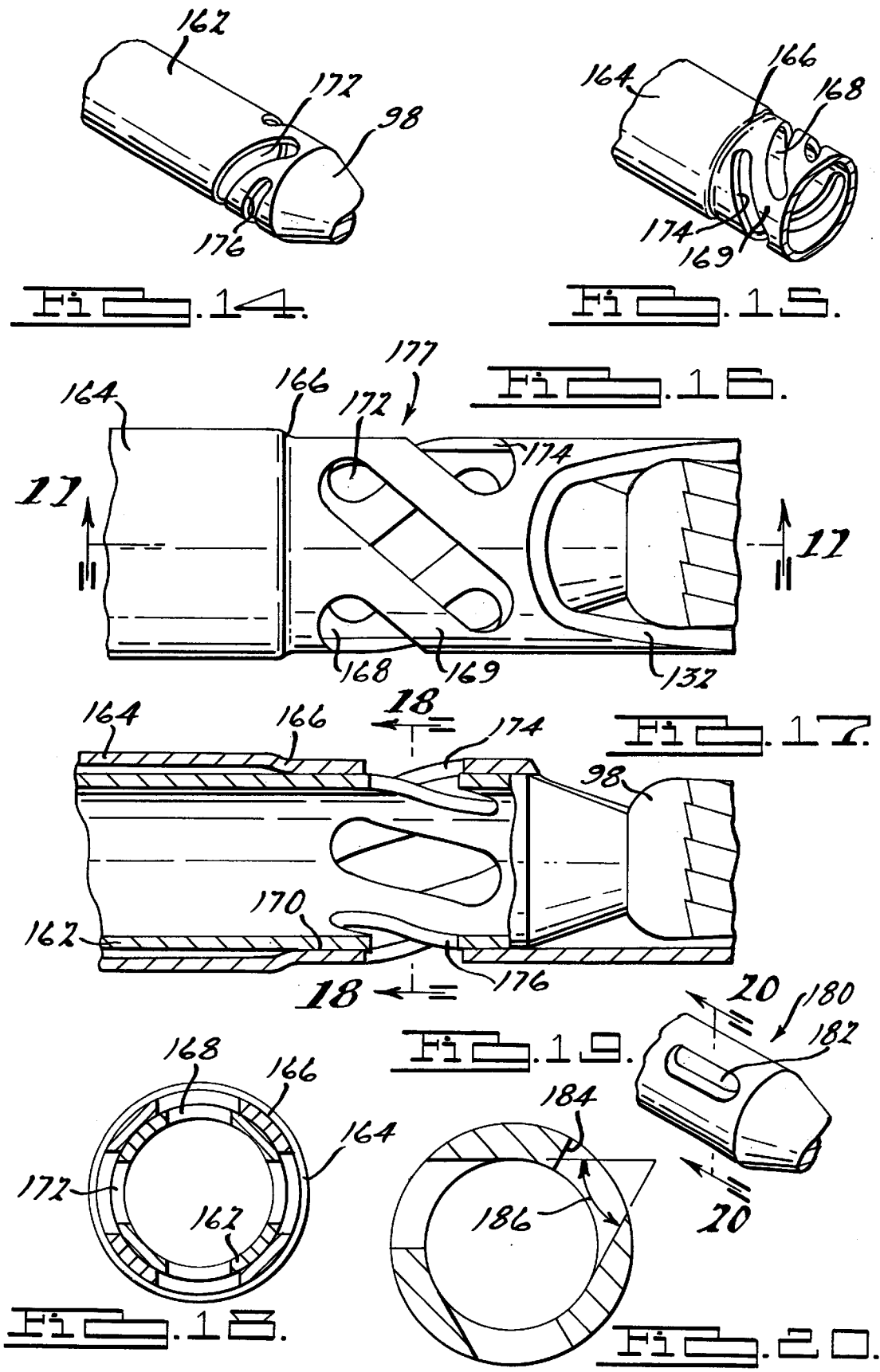

METHOD AND APPARATUS FOR ABRADING TISSUE

BACKGROUND OF THE INVENTION

1. Field of the Invention

This invention relates generally to a method and apparatus for use in arthroscopic surgical procedures, and more particularly to a method and apparatus for abrading tissue during arthroscopic surgical procedures.

2. Discussion of the Related Art

Arthroscopic or endoscopic surgery is a minimally invasive therapeutic and/or diagnostic procedure in which relatively small visualization and surgical tools are introduced into a portion of the human body such as a knee or shoulder joint through relatively small incisions made within the body. Typically, at least three (3) incisions are employed for a therapeutic procedure and at least two (2) incisions are employed for a diagnostic procedure. During arthroscopic surgery, physiological fluid such as a sterile saline solution is allowed to flow through the desired joint so as to distend the joint to facilitate access to this surgical site. In addition, the flow of physiological fluid through the joint enhances the clarity of the field of view by removing debris from the surgical site.

One of the surgical tools generally employed in arthroscopic surgery is a shaver handpiece having a suction tube. Shaver blades having hollow bores are typically removably coupled to the shaver handpiece and are used for cutting, resecting, boring and abrading both soft and hard tissue at the surgical site. An abrader shaver blade generally includes a rotatable inner tube having an abrading head at its distal end and a fixed outer tube for rotatably receiving the inner tube. Abraders are used for abrading or shaping both soft and hard tissue such as bone, cartilage, ligaments, etc. by use of the rotating abrading head. As the tissue is being abraded, debris is generally drawn or sucked through the rotatable inner tube along with the physiological fluid.

This flow of debris through the abrader, however, may clog the flow path through the inner tube. For example, U.S. Pat. No. 4,842,578 to Johnson, et al. discloses an abrader having a distal abrading head, an internal suction port located proximally from the abrading head and a bearing surface positioned proximal from the suction port. The fluid and debris flows past the abrading head, between or within the inner and outer tubes, into the internal suction port and out the inner tube at its proximal end. However, should a large quantity or large size debris be displaced by the abrading head, the internal suction port located between the inner and outer tubes may become clogged due to the confined space in this region. Moreover, this abrader does not provide a means to automatically unclog or self-clean the internal suction port should this condition occur. Accordingly, this clogging condition is somewhat common in the current commercially available abraders since they only provide internal suction ports located in a confined space.

What is needed then is a method and apparatus for abrading tissue which does not suffer from the abovementioned disadvantages. This in turn, will reduce or eliminate plugging or clogging of arthroscopic abraders, reduce or eliminate the need for manually unclogging the abrader, provide an abrading surface and an aspiration port within the field of view of the surgeon, increase the efficiency of the surgical procedure, and reduce the time and cost of the surgical procedure. It is, therefore, an object of the present invention to provide such a method and apparatus for abrading tissue during arthroscopic surgical procedures.

SUMMARY OF THE INVENTION

In accordance with the teachings of the present invention, a method and apparatus for abrading tissue during arthroscopic surgery is disclosed. This is basically achieved by providing a first rotatable tube assembly having an abrading head, a second tube assembly having an external aspiration port passing through a sidewall of the second tube assembly, and a self-cleaning mechanism that is operable to self-clean the aspiration port to pass fluid and debris.

In one preferred embodiment, an apparatus for abrading tissue during arthroscopic procedures includes a first rotatable tube assembly having a first proximal end and a first distal end with an abrading head at the first distal end. The apparatus further includes a second tube assembly having a second proximal end and a second distal end with the second tube assembly being positioned substantially concentric with the first rotatable tube assembly. A cleaning mechanism is operable to clean an aspiration port in the apparatus to pass fluid and debris.

In another preferred embodiment, an apparatus for abrading tissue during arthroscopic surgical procedures includes a first rotatable tube assembly having a first proximal end and first distal end with an abrading head at the first distal end. The apparatus further includes a second tube assembly having a second proximal end and a second distal end and defining an external aspiration port passing through a sidewall of the tube assembly such that the aspiration port is operable to pass fluid and debris.

In another preferred embodiment, an apparatus for abrading tissue during arthroscopic surgical procedures includes a first rotatable tube assembly having a first proximal end and a first distal end with an abrading head at the first distal end and an internal aspiration port adjacent to the abrading head. The apparatus further includes a second tube assembly having a second proximal end and second distal end with an internal bearing surface adjacent to the second distal end and an external aspiration port positioned substantially proximal to the internal bearing surface. The first rotatable tube assembly is operable to be rotatably positioned substantially within the second tube assembly so that the internal and external aspiration ports cooperate whereby a flow of fluid and debris from about the abrading head is operable to flow outside the second tube assembly and into the internal and external aspiration ports without substantially clogging the internal and external aspiration ports.

Use of the present invention provides a method and apparatus for abrading tissue during arthroscopic surgical procedures. As a result, the aforementioned disadvantages associated with the currently available methods and techniques for abrading tissue during arthroscopic surgical procedures have been substantially reduced or eliminated.

BRIEF DESCRIPTION OF THE DRAWINGS

Still other advantages of the present invention will become apparent to those skilled in the art after reading the following specification and by reference to the drawings in which:

FIG. 2 is a side elevational view of an inner tube assembly of an apparatus for abrading tissue according to the teachings of a first preferred embodiment of the present invention;

FIG. 3 is a side elevational view of an outer tube assembly of the apparatus for abrading tissue according to the teachings of the first preferred embodiment of the present invention;

FIG. 4 is an assembled cross-sectional view of the apparatus for abrading tissue as shown in FIGS. 2 and 3;

FIG. 5 is an enlarged perspective view of an internal aspiration port of the inner tube assembly shown in FIG. 2;

FIG. 6 is an enlarged perspective view of an external aspiration port of the outer tube assembly shown in FIG. 3;

FIG. 7 is an enlarged distal end view of the apparatus for abrading tissue;

FIG. 8 is an enlarged partial cross-sectional view of the apparatus for abrading tissue shown in FIG. 7 taken along line 8—8 of FIG. 7;

FIG. 9 is a longitudinal cross-section of the apparatus for abrading tissue taken along line 9—9 of FIG. 8;

FIG. 10 is an elevational view of the apparatus for abrading tissue according to the teachings of the first preferred embodiment of the present invention shown in use;

FIG. 11 is a side elevational view of an inner tube assembly of an apparatus for abrading tissue according to the teachings of a second preferred embodiment of the present invention;

FIG. 12 is a side elevational view of an outer tube assembly of the apparatus for abrading tissue according to the teachings of the second preferred embodiment of the present invention;

FIG. 13 is an assembled cross-sectional view of the apparatus for abrading tissue shown in FIGS. 11 and 12;

FIG. 14 is an enlarged perspective view of an internal aspiration port of the inner tube assembly shown in FIG. 11;

FIG. 15 is an enlarged perspective view of an external aspiration port of the outer tube assembly shown in FIG. 12;

FIG. 16 is an enlarged distal end view of the apparatus for abrading tissue;

FIG. 17 is an enlarged partial cross-sectional view of the apparatus for abrading tissue taken along line 17—17 of FIG. 16;

FIG. 18 is a longitudinal cross-section of the apparatus for abrading tissue taken along line 18—18 of FIG. 17;

FIG. 19 is an enlarged perspective view of an internal aspiration port of an inner tube assembly according to the teachings of a third preferred embodiment of the present invention; and FIG. 20 is a longitudinal cross-section of the internal aspiration port of FIG. 19 taken along lines 20—20 of FIG. 19.

DETAILED DESCRIPTION OF THE PREFERRED EMBODIMENT(S)

Figure 1:
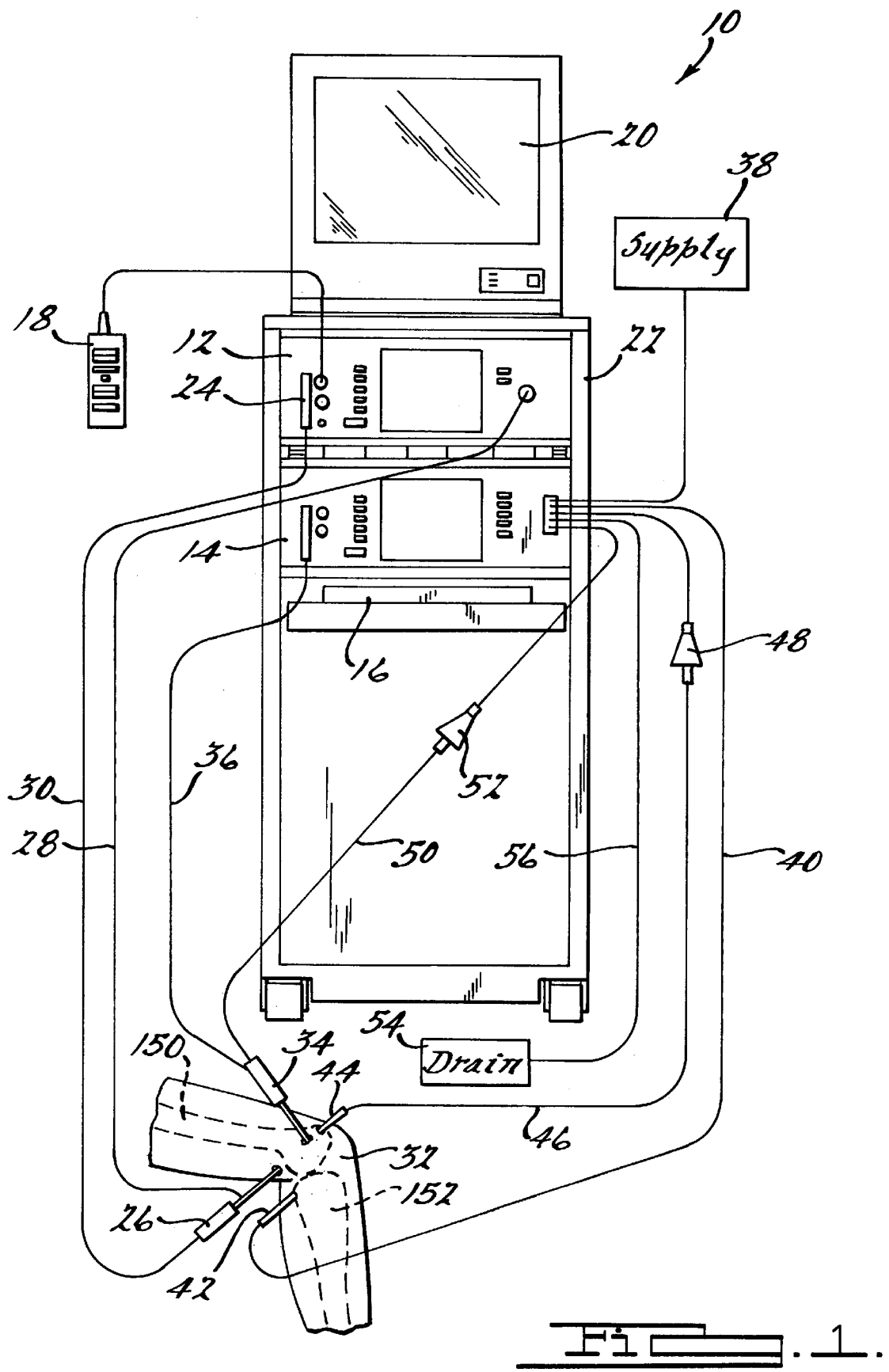
FIG. 1 is a front elevational view of an apparatus for performing arthroscopic surgical procedures.

The following description of the preferred embodiments concerning a method and apparatus for abrading tissue during arthroscopic surgery are merely exemplary in nature and are not intended to limit the invention or its application or uses. Moreover, while the present invention is described in detail below with reference to performing arthroscopic surgery on a knee joint, it will be appreciated by those skilled in to the art that the present invention is clearly not limited to merely arthroscopic surgery of the knee joint but may involve arthroscopic or other surgery at any portion of the human body. It should further be noted that any specific dimensions disclosed herein are merely exemplary in nature and may vary depending on the type of arthroscopic procedure being performed and the patient's size and needs.

Referring to FIG. 1, an apparatus 10 for performing arthroscopic surgical procedures is shown. The apparatus 10 includes an imaging unit 12, an intra-articular unit 14, a keyboard 16, an autoclavable remote control unit 18, a video monitor 20, and a cart 22. The imaging unit 12 includes a camera 24 which receives optical signals from a camera head 26, via a fiber optic cable 28 and an electrical cord 30. The imaging unit 12 is used for viewing a surgical site or a distended joint area 32 which may be viewed on the video monitor 20.

The intra-articular unit 14 provides and controls the inflow and outflow of fluid to the surgical site 32 and drives a shaver handpiece 34, via an electrical cord 36. Fluid from a fluid supply 38 is supplied, via tube 40 and inflow cannula 42. Fluid is removed or withdrawn from the surgical site 32 either by means of an outflow cannula 44 and tube 46 having a filter 48 or through the shaver handpiece 34, tube 50 and filter 52. This fluid and debris is then delivered to a drain reservoir 54, via an outflow tube 56.

A more detailed description of the apparatus 10 is set forth in U.S. Pat. No. 5,685,821 to Pike, which is hereby incorporated by reference. Moreover, it should be noted that the apparatus 10 is merely an exemplary apparatus for use in performing arthroscopic surgery. It will understood that various other apparatus for performing arthroscopic surgery can also be employed with the preferred embodiments of the present invention.

Turning now to FIGS. 2–10, an apparatus or abrader 60 for abrading tissue during arthroscopic surgical procedures is disclosed. The apparatus 60 has a proximal end 62 which is coupled to the shaver handpiece 34 and a distal end 64 which performs the abrading of the tissue at the surgical site 32. The apparatus 60 comprises an inner tube assembly 66 (see FIG. 2) and an outer tube assembly 68 (see FIG. 3). The inner and outer tube assembles 66 and 68 are preferably constructed from stainless steel or other suitable biocompatible material that may be autoclavable. Alternatively, should a disposable apparatus 60 be desired, select portions of the apparatus 60 may be constructed from polymer materials.

Referring specifically to FIGS. 2 and 4, the inner tube assembly 66 includes a drive member or assembly 70, an inner suction tube 72 and an abrader head 74. The drive assembly 70 is preferably made from a polymer material should a disposable apparatus 60 be desired, otherwise it is constructed of a stainless steel or aluminum. The drive assembly 70 is located at the proximal end 62 and has a first cylindrical sidewall 76, a second cylindrical sidewall 78 with a shoulder 80 located there between. The first cylindrical sidewall 76 fixedly retains a first cylindrical tubular portion 82 of the inner tube 72 by any appropriate fixation means such as adhesive, insert molding or ultrasonic staking. The second cylindrical sidewall 78 defines a plurality of scalloped members 84 which are engaged by the shaver handpiece 34 to axially rotate the inner tube assembly 66. Captured between the first tubular portion 82 and the second cylindrical sidewall 78 is a resilient spring 86 which is used to maintain the axial position of the inner tube assembly 66 relative to the outer tube assembly 68 during rotation of the inner tube assembly 66 in relation to the fixed outer tube assembly 68.

The inner tube 72 further includes a second cylindrical tubular portion 88 extending from a shoulder 90 having an outer diameter which is slightly smaller than the outer diameter of the first tubular portion 82. The second tubular portion 88 includes a conical transition region 92 which extends into a third cylindrical tubular portion 94 having an outer diameter which is substantially the same as the first tubular portion 82. The third tubular portion 94 defines a pair of transversely aligned aspiration or suction ports 96 located substantially adjacent to the distal end 64 of the inner tube assembly 66. From the third tubular portion 94 extends a solid conical transition region 98 having an angle of about 22.5° degrees per side coupled to the abrader head 74. The inner tube 72 along with the abrader head 74 is preferably machined from two pieces of stock and sleeved and welded along joint 99. Alternatively, the abrader head 74 and the inner tube 72 may be machined from a single piece of stock or other suitable machined assembly can also be used. Moreover, the abrader head 74 may be elongated as shown, or have any other desired shape such as round, etc. The inner tube 72 also includes a substantially cylindrical elongated inner sidewall 100 defining an elongated bore 102 having an open proximal end 104 and a closed distal sidewall end 106.

Referring now to FIGS. 3 and 4, the outer tube assembly 68 includes a coupling member or assembly 108 located at the proximal end 62 and an outer elongated cylindrical tube 110 fixedly retained within the coupling assembly 108. Here again, should a disposable apparatus 60 be desired, the coupling member 108 is preferably made from a polymer material, otherwise the member 108 is made of stainless steel or aluminum. The coupling assembly 108 includes a tapered body 112 having an engagement groove 114 about its circumference for removably coupling the coupling assembly 108 to a quick-release chuck of the shaver handpiece 34. Located at the proximal end 62 of the coupling assembly 108 is a substantially cylindrical portion 116 having a plurality of scalloped members 118. A seal 120 is retained about the circumference of the cylindrical portion 116 and captured within a groove 122. The seal 120 is used to fluidly seal the coupling assembly 108 relative to the quick-release chuck of the shaver handpiece 34. The coupling assembly 108 further defines a substantially cylindrical counter-bore 124 which is operable to rotatably receive the driving assembly 70. Located at the end wall 125 of the counter bore 124 is an annular flanged bearing 126 that the first outer tubular portion 82 rotatably rides within. The outer tube 110 also includes a single aspiration or suction port 128 having guard members 130 positioned substantially adjacent to the distal end 64. The outer cylindrical tube 110 further includes a tapered or angled shield 132 which tapers at an angle of about 15° degrees to expose a portion of the abrader head 74.

Referring to FIGS. 4 and 8, the outer tube 110 further includes a first inner cylindrical sidewall 134 having a first diameter of about 4.7 millimeters and a second inner cylindrical sidewall or bearing surface 136 having a second diameter of about 4.6 millimeters with a stepped shoulder 138 positioned there between. The first inner cylindrical sidewall 134 provides a clearance of about 0.2 millimeters per side between the inner cylindrical sidewall 134 and the second tubular portion 88 and a clearance of about 0.065 millimeters per side between the inner cylindrical sidewall 134 and the third tubular portion 94. The additional clearance provided near the proximal end 62 is used to prevent binding between the inner tube assembly 66 with the outer tube assembly 68 due to any flexing that may occur in this region as a surgeon is performing the abrading. In other words, the moment arm or line of force generally falls within this region of the proximal end 62 during abrading, thereby requiring the additional clearance in this region.

The second inner sidewall 136 has a smaller diameter than the first inner sidewall 134 in order to act as a distal bearing surface 136 relative to the inner tube 72. In this way, the bearing surface 136 is located distally from the suction ports 96 and 128 with the distal end of the third tubular portion 94 rotatably riding within this bearing surface 136 having a clearance of about 0.02 millimeters per side. The outer tube 110 may be formed by the use of a first tube 140 having an inner diameter corresponding to the inner sidewall 134 and a second tube or bearing member 142 having an inner diameter corresponding to the inner bearing sidewall or surface 136. Each tube 140 and 142 are then axially aligned concentric with one another and welded together thereby creating the inner stepped shoulder 138. The outer cylindrical surface of the tube 110 may then be machined so that the outer cylindrical surface has a substantially uniformed diameter throughout its axial length. Alternatively, a single tube 110 may be used where the distal end 64 is merely swaged to form the bearing member 142, such that the inner diameter is reduced to form the inner bearing surface 136 which will thereby provide a rounded shoulder versus the stepped shoulder 138, as shown in FIG. 8.

Referring now to FIGS. 5–9, an automatic self-cleaning mechanism 143 of the preferred embodiment of the present invention will now be discussed. Each internal suction port 96 is defined by a substantially oval shaped sidewall 144 having a plurality of scalloped teeth 146. The external suction port 128 is also defined by a substantially oval sidewall 148. The sidewall 144 and the sidewall 148 are each cut to form opposing cutting planes relative to one another and sharpened along these planes to create a scissor-like self-cleaning cutting mechanism 143. In other words, as the internal suction ports 96 rotate relative to the fixed external suction port 128, the sharpened scalloped teeth 146 in relation to the fixed sharpened sidewall 148 act as a cutting or scissor mechanism 143 to chop or cut debris as it is drawn into the bore 102. As the cutting action is occurring across the suction port 128, the guard members 130 prevent unwanted cutting of tissue adjacent the external suction port 128 when the abrader 60 is abrading in tight clearance areas.

In operation, the joint at the surgical site 32 is distended by irrigating the area, via the fluid supply 38, intra-articular unit 14 and the inflow cannula 42 coupled to the inflow tube 40. With the joint being distended, the camera head 26 enables viewing at the surgical site 32 within a field of view of the camera head 26, while the outflow cannula 44 coupled to the outflow tube 46 and drain reservoir 54 removes the fluid from the surgical site 32. Should it be desired to abrade a hard surface of the femur 150, the tibia 152, cartilage or soft tissue in this region, the shaver handpiece 34 having the abrader 60 coupled thereto is inserted into the surgical site 32 as shown in FIG. 10. However, one skilled in the art would recognize that the abrader 60 may also be used for shoulder arthroscopic surgery, as well as any other forms of surgery. With the abrader 60 being inserted into this region, the speed of the inner tube assembly 66 is adjusted between about 3000 to 4000 RPMs and the outflow of the physiological fluid is drawn through the shaver handpiece 34 at a rate of about 500 to about 600 milliliters per minute.

The rotating abrader head 74 which has a plurality of helically shaped teeth 154 is engaged with the desired area to be shaped such as the inner or outer condyle of the femur 150. Upon shaping or abrading this area, debris 156 is drawn from the distended joint region 32, out and around the inner bearing surface 136 or member 142, down into the external suction port 128, and through the internal suction ports 96 along flow path 158. As the debris 156 is drawn through the suction ports 128 and 96, the corresponding scalloped teeth 146 and sidewall 148 act to cut and chop the debris 156 such that the debris is able to flow easily within the suction ports 128 and 96 along the inner bore 102 without clogging the inner bore 102.

The flow path 158 of fluid and debris 156 is substantially prohibited between the inner bearing surface 136 and the third tubular portion 94. However, a thin film of fluid will be formed between this region to act as a lubricant in this bearing area. The flow path 158 of fluid and debris 156 is from the abrader head 74 to outside the outer tube 110, around the bearing surface 136 and into the substantially large external suction port 128 having guard members 130. This flow path 158, along with the self-cleaning mechanism 143 having the cooperating sidewalls 148 and 144 provides an abrader 60 which is able to remove debris 156 without being substantially plugged or clogged and also provides automatic self-cleaning should large portions of debris 156 be drawn adjacent to the exterior suction port 128. In other words, should a large piece of debris 156 which would normally clog an abrader be dislodged and drawn to the exterior suction port 128, this piece of debris 156 will be chopped into many smaller pieces as it is drawn through the exterior suction port 128 and chopped by the pair of rotating interior suction ports 96 having the scalloped teeth 146.

In addition, by providing the substantially angled portion 98, as well as positioning the exterior suction port 128 and the interior suction ports 96 substantially adjacent to the distal end 64 or substantially adjacent to the abrader head 74, the abrader 60 is also able to remove and draw in substantially all the debris 156 displaced by the abrader head 74, via the flow path 158. This compact positioning of the abrader head 74 substantially adjacent to the external suction port 128 and the internal suction ports 96 also provides an additional benefit of enabling the surgeon to view both the abrader head 74 and the exterior suction port 128 within the field of view of the camera head 26 (see FIG. 10). In other words, by maintaining the distance between the external and internal suction ports 128, 96 and the distal end 64 of the abrader head 74 between the range of about 20 to 40 millimeters, this enables the surgeon to confirm that the self-cleaning mechanism 143 having guard members 130 is appropriately positioned within the surgical site 32 relative to other hard and soft tissue which is not desired to be abraded or cut. Moreover, this also allows substantially all the debris 156 to be drawn through the flow path 158 into the exterior suction port 128.

Turning now to FIGS. 11–18, an apparatus or abrader 160 according to the teachings of a second preferred embodiment of the present invention is shown. In this regard, like reference numerals will be used to identify like structures with respect to the first preferred embodiment of the abrader 60. The abrader 160 is substantially similar to the abrader 60 except for generally three areas. First, the inner tube 162 (see FIG. 11) is substantially cylindrical and one-piece throughout its length and does not include the smaller diameter at the second tubular portion 88 or the tapered portion 92, as shown in FIG. 2, which provides the additional clearance area to prevent binding in the first preferred embodiment. In order to provide this additional clearance, the outer tube 164 (see FIG. 12) has an enlarged diameter substantially throughout its length up to a tapered shoulder 166. This enlarged diameter provides a clearance of about 0.2 millimeters per side substantially throughout the length of the outer tube 164 up to the shoulder 166 in order to provide sufficient clearance for flexing of the inner tube 162 relative to the outer tube 164.

Second, the bearing surface in this embodiment extends substantially from the shoulder 166 which is proximal to a plurality of external suction ports 168 up to the distal end 64. This elongated bearing surface is formed by an inner bearing sidewall or surface 170 of the outer tube 164. This bearing surface 170 is created by simply swaging the distal end 64 of the outer tube 164 down to a smaller inner and outer diameter.

Finally, the external aspiration or suction ports 168 having guards 169, as well as a plurality of internal aspiration or suction ports 172 are shaped as opposed helical grooves. This configuration provides aspiration or suction substantially about the entire circumference of the outer tube 164 adjacent to the distal end 64. Here again, the external suction ports 168 are defined by (1) helical sidewalls 174 and the internal suction ports are defined by (2) helical sidewalls 176 which cooperate relative to one another in a scissor-like action to form a self- cleaning mechanism 177.

It should be noted that in this embodiment, the inner bearing surface 170 extends proximal from the exterior suction ports 168 out to the distal end 64 in order to ensure a proper scissor-like action or clearance between the external suction ports 168 and the internal suction ports 172. In other words, since the clearance between the inner tube 162 and the outer tube 164 is enlarged to about 0.2 millimeters per side which is larger than the clearance observed between the external suction port 128 and the internal suction ports 96, shown clearly in FIG. 8, the bearing surface 170 in this embodiment extends throughout the suction port region.

In operation, the fluid path of the abrader 160 is substantially similar to the fluid path 158 of the abrader 60 such that fluid and debris 156 will flow from the abrading head 74 out and around a portion of the bearing surface 170 and back through the external suction ports 168 with any large debris being cut by the action of the internal suction ports 172 relative to the external suction ports 168. This embodiment thereby provides additional clearance for the inner tube 162 relative to the outer tube 164, as well as provides suction from about the entire circumference of the outer tube 164 which may be desirable in some abrading applications.

Turning now to FIGS. 19 and 20, a third preferred embodiment of an internal aspiration port 180 is shown. The internal aspiration port 180 includes three (3) longitudinal extending slots 182 positioned at 120° degrees relative to one another about either of the inner tubes 72 or 162. The longitudinal slots 182 are defined by (3) longitudinally extending angled sidewalls 184 which angle in at about 60° degrees, identified by reference numeral 186. The internal aspiration or suction port 180 is preferably designed to cooperate with the external suction port 168, however, the external suction port 128 may also be used. The internal aspiration port 180 having angled sidewalls 184 cooperates with either the external aspiration port 168 or 128 to form a self-cleaning mechanism which is operable to chop debris 156 as it is drawn into the external 168/128 and internal aspiration ports 180. In addition, by angling the sidewalls 184, as shown in FIG. 20, upon rotating the inner tube 72 or 162 counter-clockwise, the internal aspiration port 180 further acts as an impeller to provide additional suction thereby assisting in the withdrawal of fluid and debris 156 from the surgical site 32.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. An apparatus for abrading tissue during arthroscopic surgical procedures, said apparatus comprising:

a first inner rotatable tube assembly having a first proximal end and a first distal end, said first inner rotatable tube assembly having an abrading head at said first distal end and an internal aspiration port defined by at least a first sidewall, said internal aspiration port being positioned proximal said abrading head;

a second outer tube assembly having a second proximal end and a second distal end, said second outer tube assembly having an external aspiration port defined by at least a second sidewall; and said internal aspiration port being rotatably positioned substantially adjacent to said external aspiration port, wherein upon rotating said first rotatable tube assembly, said first sidewall cooperates with said second sidewall to cut debris as the debris and fluid is drawn into and passes through said external and internal aspiration ports.

2. The apparatus as defined in claim 1 wherein said internal and external aspiration ports are positioned substantially adjacent to said first distal end and said second distal end, respectively, whereby said external aspiration port and said abrading head are located substantially adjacent to one another to be substantially within a field of view of a surgeon during the arthroscopic surgical procedure.

3. The apparatus as defined in claim 1 wherein said first sidewall defining said internal aspiration port and said second sidewall defining said external aspiration port are sharpened to form a scissor-like cutting mechanism upon rotating said first inner rotatable tube assembly relative to said second outer tube assembly.

4. The apparatus as defined in claim 2 wherein said first sidewall defining said internal aspiration port includes a plurality of sharpened scalloped teeth.

5. The apparatus as defined in claim 1 wherein said external aspiration port includes at least one guard member operable to prevent unwanted cutting of fixed tissue.

6. The apparatus as defined in claim 1 wherein said internal aspiration port includes a pair of transversely aligned ports.

7. The apparatus as defined in claim 1 wherein said internal aspiration port is defined by a plurality of helical sidewalls positioned about a circumference of said first inner rotatable tube assembly and said external aspiration port is defined by a plurality of opposed helical sidewalls positioned about a circumference of said second outer tube assembly.

8. The apparatus as defined in claim 1 wherein said internal aspiration port includes a plurality of longitudinal extending angled sidewalls, wherein said internal aspiration port having said plurality of longitudinal extending angled sidewalls is operable to act as an impeller to withdraw fluid and debris through said external and internal aspiration ports.

9. The apparatus as defined in claim 1 wherein said second tube assembly includes an inner bearing surface adjacent to said second distal end whereby said external aspiration port is positioned substantially proximal from said inner bearing surface.

10. The apparatus as defined in claim 1 wherein said first inner rotatable tube assembly substantially rotates within said second outer tube assembly whereby an enlarged clearance is provided between said first and second tube assemblies adjacent to said first and second proximal ends to provide for flexing of said first and second tube assemblies.

11. An apparatus for abrading tissue during arthroscopic surgical procedures, said apparatus comprising;

a first inner rotatable tube assembly having a first proximal end and a first distal end, said first inner rotatable tube assembly having an abrading head at said first distal end and an internal aspiration port defined by at least a first sidewall, said internal aspiration port being positioned proximal said abrading head; and a second outer tube assembly having a second proximal end and a second distal end, said second outer tube assembly defining an opening for exposing at least a portion of said abrading head and a separate external aspiration port passing through a sidewall of said second outer tube assembly, wherein said separate external aspiration port cooperates with said internal aspiration port to draw in fluid and cut debris.

12. The apparatus as defined in claim 11 wherein said external aspiration port is positioned substantially adjacent to said second distal end.

13. An apparatus for abrading tissue during arthroscopic surgical procedures, said apparatus comprising:

a first inner rotatable tube assembly having a first proximal end and a first distal end, said first inner rotatable tube assembly having an abrading head at said first distal end d an internal aspiration port defined by at least a first sidewall, said internal aspiration port being positioned proximal said abrading head; and a second outer tube assembly having a second proximal end and a second distal end, said second outer tube assembly defining an opening exposing at least a portion of said abrading head and an external aspiration port passing through a sidewall of said second outer tube assembly, said external aspiration port is positioned substantially about a circumference of said second tube assembly, wherein said external aspiration port cooperates with said internal aspiration port to draw in fluid and cut debris.

14. The apparatus as defined in claim 11 wherein said internal aspiration port and said external aspiration port each have sharpened sidewalls that cooperate to form a self-cleaning mechanism operable to cut debris as said debris passes through said external and said internal aspiration ports.

15. An apparatus for abrading tissue during arthroscopic surgical procedures, said apparatus comprising:

a first inner rotatable tube assembly having a first proximal end and a first distal end, said first inner rotatable tube assembly having an abrading head at said first distal end and an internal aspiration port defined by at least a first sidewall, said internal aspiration port being positioned proximal said abrading head; and a second outer tube assembly having a second proximal end and a second distal end, said second outer tube assembly defining an opening for exposing at least a portion of said abrading head and an external aspiration port passing through a sidewall of said second outer tube assembly; and an inner bearing surface positioned substantially adjacent said second distal end such that said external aspiration port is positioned proximally from said inner bearing surface, wherein said external aspiration port and said internal aspiration port cooperate to draw in fluid and cut debris.

16. An apparatus for abrading tissue during arthroscopic surgical procedures, said apparatus comprising:

a first inner rotatable tube assembly having a first proximal end and a first distal end, said first inner rotatable tube assembly having an abrading head at said first distal end and an internal aspiration port substantially adjacent to said abrading head; and a second outer tube assembly having a second proximal end and a second distal end, said second outer tube assembly having an inner bearing surface substantially adjacent to said second distal end and an external aspiration port substantially proximal to said inner bearing surface, wherein said first inner rotatable tube assembly is operable to be rotatably positioned substantially within said second outer tube assembly whereby said external aspiration port cooperates with said internal aspiration port to form a scissor-like self-cleaning mechanism which is operable to cut and chop debris amid debris and fluid is drawn into said external and internal aspiration ports.

17. The apparatus as defined in claim 16 wherein said inner bearing surface extends longitudinally along said external aspiration port.

\* \* \* \* \*

UNITED STATES PATENT AND TRADEMARK OFFICE
CERTIFICATE OF CORRECTION

PATENT NO. : 6,053,923
DATED : April 25, 2000
INVENTOR(S) : John J. Veca

It is certified that error appears in the above-identified patent and that said Letters Patent is hereby corrected as shown below:

Title page,
Item [56], Reference Cited, Foreign Priority Data, "2007239" UK should be -- 2087239 -- and delete duplicate listing of "2093353  9/1982 UK"

Item [56], Reference Cited, OTHER PUBLICATIONS,
delete duplicate listing of "MicroAire Advanced Surgical Products, ..."

ABSTRACT,
Line 4, "rotatably" should be -- rotatable --.

Column 1,
Lines 58-59, "abovementioned" should be -- above mentioned --.

Column 3,
Line 58, delete "to".

Column 5,
Lines 5 and 43, delete "degrees"

Column 8,
Line 10, delete "(1)".
Line 11, delete "(2)".
Lines 40 and 44, delete "degrees".
Line 42, delete "(3)".

Column 9,
Line 65, "comprising;" should be -- comprising: --

Column 10,
Line 21, "d" should be -- and --.
Lines 66-67, delete "substantially adjacent to" & substitute -- being positioned proximal --.

UNITED STATES PATENT AND TRADEMARK OFFICE
CERTIFICATE OF CORRECTION

PATENT NO. : 6,053,923
DATED : April 25, 2000
INVENTOR(S) : John J. Veca

It is certified that error appears in the above-identified patent and that said Letters Patent is hereby corrected as shown below:

<u>Column 12,</u>
Line 3, "amid" should be -- as said --.

Signed and Sealed this

Thirtieth Day of April, 2002

Attest:

JAMES E. ROGAN
*Attesting Officer*     *Director of the United States Patent and Trademark Office*